United States Patent [19]

Blecha et al.

[11] Patent Number: 5,830,993
[45] Date of Patent: Nov. 3, 1998

[54] SYNTHETIC ANTIMICROBIAL PEPTIDE

[75] Inventors: Frank Blecha; Jishu Shi, both of Manhattan, Kans.

[73] Assignee: Kansas State University Research Foundation, Manhattan, Kans.

[21] Appl. No.: 419,066

[22] Filed: Apr. 10, 1995

[51] Int. Cl.⁶ .............................. A61K 38/00; C07K 14/00
[52] U.S. Cl. ......................... 530/300; 530/324; 530/350; 514/2
[58] Field of Search ................................. 514/2; 530/300, 530/350, 324

[56] References Cited

U.S. PATENT DOCUMENTS

| | | |
|---|---|---|
| 5,028,530 | 7/1991 | Lai et al. . |
| 5,034,510 | 7/1991 | Shiba et al. . |
| 5,106,735 | 4/1992 | Natori et al. . |
| 5,118,789 | 6/1992 | Natori . |
| 5,166,321 | 11/1992 | Lai et al. . |
| 5,202,420 | 4/1993 | Zasloff et al. . |
| 5,206,154 | 4/1993 | Lai et al. . |
| 5,324,716 | 6/1994 | Selsted et al. . |

FOREIGN PATENT DOCUMENTS 9609322  3/1996  WIPO .

OTHER PUBLICATIONS

Shi, et al.; Identification of a Proline–Arginine–Rich Antibacterial Peptide from Neutrophils that is Analogus to PR–39, an Antibacterial Peptide from the Small Intestine; Journal of Leukocyte Biology; vol. 56, No. 6, Dec. 1994, pp. 807–811.

Agerberth et al.; Amino Acid Sequence of PR–39; Eur. J. Biochecm. 202, 849–854.

*Primary Examiner*—Paula K. Hutzell
*Assistant Examiner*—Khalid Masood
*Attorney, Agent, or Firm*—Hovey, Williams, Timmons & Collins

[57] ABSTRACT

New antimicrobial truncated peptides are disclosed which are based upon a known peptide, PR-39 (SEQ ID NO: 1) but which contain a lesser number of amino acid residues yet still retain antimicrobial activity. The most preferred peptide compound is PR-26, SEQ ID NO: 2. The invention also relates to a method of inhibiting microbial growth by administering an effective amount of a peptide in accordance with the invention.

2 Claims, 6 Drawing Sheets

SYNTHETIC ANTIMICROBIAL PEPTIDE

BACKGROUND OF THE INVENTION

1. Field of the Invention

The present invention is broadly concerned with antimicrobial peptides which can be used for inhibiting microbial growth. More particularly, the invention is concerned with truncated peptides based upon a known, naturally occurring proline-arginine (PR)-rich antimicrobial protein known as PR-39.

2. Description of the Prior Art

Infectious diseases are a primary cause of morbidity and mortality in humans and animals. These maladies range from the troublesome, e.g., E. coli diarrhea which is caused by the consumption of contaminated food and drinks, to the deadly, e.g., AIDS.

A variety of antimicrobial agents have been developed to combat infectious diseases. Recently, several types of antimicrobial peptides have been discovered. Such peptide antimicrobials are produced by many biological organisms (Gabay, 1994) and are important components of host defense mechanisms (Zasloff, 1992; Boman, 1991). For example, defensins are expressed in several mammalian species (Lehrer, Lichtenstein, and Ganz, 1993), magainins have been identified in the skin and intestine of frogs (Zasloff 1987; Moore et al., 1992), and cecropins have been isolated from insects and pigs (Steiner, et al., 1981; Lee et al., 1989). These natural antimicrobials are lytic peptides that kill microorganisms by pore-forming, membrane-damaging mechanisms (Boman, Agerberth, and Boman, 1993; Maloy and Prasad Kari, 1995).

Recently, a group of proline-arginine (PR)-rich antibacterial peptides have been identified. Bactenecin 5 and 7 have been isolated from bovine neutrophils (Gennaro et al., 1989; Litteri and Romeo, 1993) and PR-39 was first isolated from the porcine small intestine (Agerberth et al., 1991) and identified recently in porcine neutrophils (Shi et al., 1994b). Although these PR-rich antibacterial peptides share a similar high content of proline (47, 47, and 49%, respectively) and arginine (21, 29, and 26%, respectively), they possess different killing mechanisms. Similar to other lytic peptides, bactenecins kill bacteria by a membrane-permeability-associated mechanism (Maloy and Prasad Kari, 1995); however, PR-39 was found to kill bacteria by interfering with DNA and/or protein synthesis (Boman, Agerberth, and Boman, 1993). Furthermore, PR-39 has been isolated from wound fluid and was shown to induce syndecan expression on mesenchymal cells (Gallo, 1994). Because syndecans are important in wound repair, this finding suggests that PR-39, in addition to its antibacterial properties, may have a larger role in inflammatory processes and tissue repair. However, little is known about the structure—function relationship of PR-39.

The patent art also discloses antimicrobial peptides. Thus, U.S. Pat. No. 5,234,716 describes broad spectrum tryptophan antimicrobial peptides. Similarly, U.S. Pat. No. 5,202,420 discloses tracheal antimicrobial peptides.

SUMMARY OF THE INVENTION

The present invention provides improved isolated peptide compounds based upon the known peptide PR-39 (SEQ ID NO: 1) but which are truncated and still retain the functional antimicrobial domain of the parent peptide. As a consequence, synthesis of the truncated peptides of the invention is more readily performed and is less costly than that of the parent peptide. As used herein, "antimicrobial" refers to the killing of microorganisms or the suppression of their multiplication and/or growth.

In preferred forms, the invention relates to isolated antimicrobial peptides comprising a peptide compound having a partial amino acid sequence of PR-39 (SEQ ID NO: 1) with at least 15 and less than all of the amino acid residues of PR-39, beginning at the —NH$_2$ terminal thereof. The single most preferred peptide compound, PR-26, has the amino acid sequence of SEQ ID NO: 2. More broadly however, the invention relates to isolated peptides having substantially the same amino acid sequence and at least substantially the same antimicrobial activity as PR-26, SEQ ID NO: 2.

The invention also includes a method of inhibiting microbial growth in an environment capable of sustaining such growth. This method comprises administering to the environment a microbial growth-inhibiting amount of a peptide in accordance with the invention.

The truncated peptides of the invention are advantageous in that they are based on the natural porcine antimicrobial peptide PR-39 and therefore have greater use and acceptability in the swine industry. The preferred PR-26 peptide is more effective in vitro than the common feed-additive antibiotic, carbadox; moreover, this peptide exhibits minimal inhibitory concentrations for S. cholerasuis much lower than that of carbadox and cecropin P1. The peptides of the invention can be used for the treatment of swine enteric diseases caused by S. cholerasuis and E. coli through oral administration of the peptides. Similarly, such diseases may be prevented by inclusion of the peptide in the swine diet. It is also believed that the peptides of the invention are useful via topical administration to enhance wound treatment.

DETAILED DESCRIPTION OF THE PREFERRED EMBODIMENT

Figure 1:
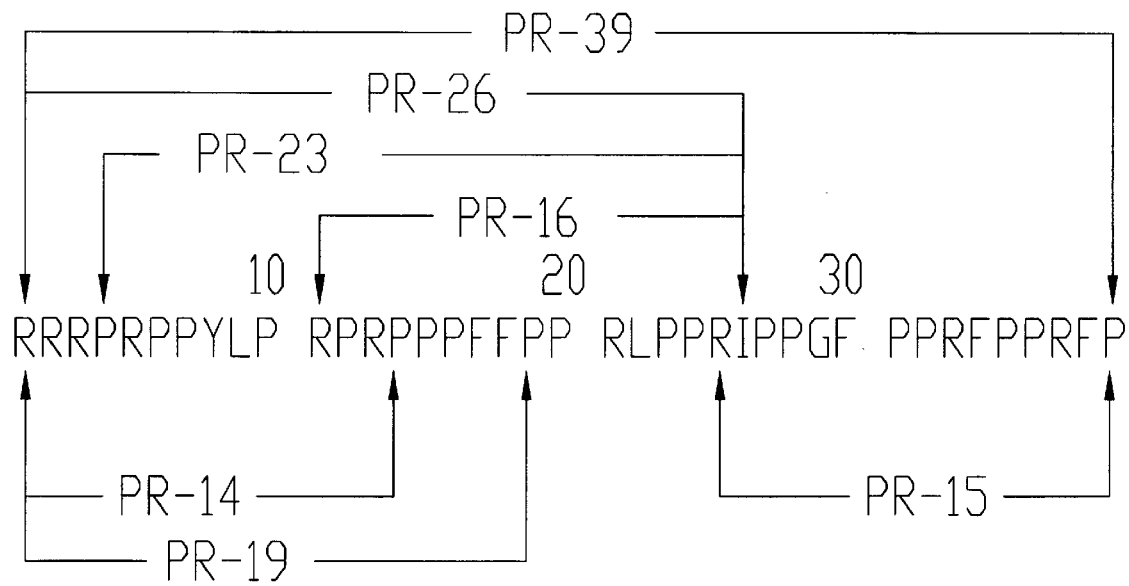
FIG. 1 is the amino acid sequence of PR-39 and various truncated analogs thereof, including PR-26, wherein the single letter amino acid code is used and the left side of the sequence listing is the —NH$_2$ terminal end.

The following example illustrates the preferred practice of the invention. It is to be understood, however, that this example is provided by way of illustration only and nothing therein should be taken as a limitation upon the overall scope of the invention.

EXAMPLE

Materials and Methods

Peptide Design and Synthesis. Theoretical predictions of peptide characteristics, relative to hydrophilicity and antigenicity, were accomplished using a computer software program (Peptide Companion, Peptide International, Louisville, Ky.). Peptides were synthesized by the solid-phase method using t-Boc chemistry with an Applied Biosystems Model 431 Peptide Synthesizer (ABI, Foster City, Calif.). Amino acid derivatives having the L-configuration were used. Peptides were purified by reversed-phase high performance liquid chromatography (RP-HPLC) and characterized by hybrid tandem mass spectrometry and acidurea-polyacrylamide gel electrophoresis (AU-PAGE) (Shi et al., 1994b).

Assays of Antibacterial Activity. Synthetic peptides were evaluated for antibacterial activity by previously described gel-overlay and "lawn-spotting" assays (Shi et al., 1994b), by determination of the minimal inhibitory concentration (MIC) and the minimal bactericidal concentration (MBC), and by determination of the postantibiotic effect (PAE) of PR-26 and PR-39 and the bacterial susceptibility to neutrophil phagocytosis by PR-26 and PR-39.

Gel-overlay assay. As described previously (Shi et al., 1994b), peptides were subjected to AU-PAGE, the acid-urea gel was overlaid with $10^6$ bacteria (*Escherichia coli*, ATCC 25922) in 3% trypticase soy broth (TSB) and 1% agarose medium, and the overlaid gel then was incubated at 37° C. for 18 hr. Bactericidal activity was indicated by a clear zone on the agarose gel.

Lawn-spotting assay. Lawns of bacteria (*E. coli*, ATTC 25922 or *Salmonella typhimurium*, KSU isolate 7) were made on sheep-blood or brain-heart-infusion agar plates. After drying at room temperature for 10 min, 5 µl of the various peptides (dissolved in 0.01% acetic acid or phosphate buffered saline (PBS) pH 7.4) and a medium control were spotted on the surface of the bacterial lawn. Plates were incubated at 37° C. for 18 hr. Bactericidal activity was indicated by a clear zone on the bacterial lawn (Shi et al., 1994b).

Minimal inhibitory concentration (MIC) and minimal bactericidal concentration (MBC). For peptides that showed antibacterial activity using the gel-overlay and lawn spotting assays, MIC and MBC were determined by the microdilution broth method (NCCLS, 1990). Briefly, 50 µl of twofold serial dilutions (128 to 0.25 µM) of synthetic peptides were dispensed into wells of 96-well tissue culture plates. Bacteria (*E. coli*, ATCC 25922; *E. coli*, K88; *Salmonella typhimurium*, fresh isolate from a dog; *S. cholerasuis* ATCC 6962; *Streptococcus suis*, fresh isolate from porcine spleen; and *Staphylococcus aureus*) from sheep-blood or brain-heart-infusion agar plates were standardized to 0.5 McFarland in demineralized water using a radiometer/sensititre (Chelsea Instrument Ltd., England). The water/bacteria suspension (100 µl) was immediately transferred to 10 ml of cation-adjusted Muller-Hinton broth and 50 µl of the bacterial suspension then were added to each well of the microtiter plate. Plates were incubated for 20 hr. at 37° C. and MIC were determined. Ten microliters of Muller-Hinton broth, bacteria suspensions also were diluted to determine the actual bacterial concentration using standard colony forming unit (CFU) counting. After determination of the MIC, 10 µl of each bacteria-peptide suspension were plated on sheep-blood or brain-heart-infusion agar plates and incubated for 24 hr. at 37° C. to determine the MBC. Minimal bactericidal concentration was considered that peptide concentration that inhibited 99.9% of the original CFU (NCCLS, 1990).

Postantibiotic effect (PAE). *Salmonella typhimurium* was used to evaluate the PAE of PR-26 and PR-39. Stationary phase bacteria were adjusted to $5 \times 10^7$ bacteria/ml in brain-heart-infusion agar and incubated with different concentrations of PR-39 or PR-26 at 37° C. for 2 hr. Control tubes without PR-peptides were treated in an identical manner to the experimental tubes. PR-26 and PR-39 were removed by centrifugation (13,600×g for 1 min) and 100 µl of the bacteria were resuspended in 0.9 ml of PR-peptide-free brain-heart-infusion agar and incubated at 37° C. Bacteria (20 µl) were diluted in sterile saline immediately after removal of the PR-peptides and then at hourly intervals, and 20 µl aliquots were spread on nutrient agar plates. Viable bacteria were counted. Tests were repeated on three different days. Postantibiotic effect was determined by calculating the difference in time required for the number of test and control bacteria to increase 1 $\log_{10}$ above the number present immediately after removal of PR-peptides from the test cultures. The results were expressed as the mean±standard deviation. A PAE greater than 30 min. was considered significant (MacKenzie and Gould, 1993).

Susceptibility to neutrophil phagocytosis. Porcine neutrophils were isolated from 6 to 8 week-old-crossbred pigs by density-gradient centrifugation and hypotonic lysis as previously described (Shi et al., 1994a). *Salmonella cholerasuis*, ATCC 6962 was used in this experiment. Bacteria were incubated with PR-39 or PR-26 for 10 min. at 37° C. Peptides were removed from the bacterial cultures by centrifugation at 13,600×g for 1 min. Bacteria were resuspended in 1 ml of PBS and 0.1 ml of bacteria was mixed with $2 \times 10^6$ porcine neutrophils. The final volume was adjusted to 0.5 ml, 15% porcine serum. Bacteria without neutrophils and neutrophils without bacteria were used as controls. Tubes were incubated at 37° C. in a reciprocating water bath at 110 oscillations/min. Aliquots of 50 µl from the experimental tubes were used to prepare slides using a Cytospin 2 centrifuge (Shandon Southern Products Ltd., England). Slides were stained with LeukoStat solutions (Fisher, Pa.). Phagocytosis was determined by microscopy at a magnification of 1,000 (BH-2, Olympus). At least 200 neutrophils were examined. The degree of phagocytosis was calculated according to the following formula: phagocytic index=( percentage of neutrophils containing at least one bacteria )×( mean number of bacteria per positive cell ) . Tests were repeated on three different days. Results were expressed as the mean±standard deviation. PR-26 was different from control, P<0.05.

Regulation of neutrophil superoxide anion production by PR-39 and PR-26. The influence of PR-39 and PR-26 on the capability of neutrophils to generate reactive oxygen intermediates was evaluated by measuring superoxide anion production as previously described (Shi, et al., 1994a). Isolated porcine neutrophils ($1\times10^6$) were incubated with various concentrations of PR-39 or PR-26 for 2 hr. at 37° C. Superoxide anion production was measured after neutrophils were stimulated with phorbol myristate acetate (PMA) at 37° C. for 20 min. In different neutrophil cultures, PR-39 and PR-26 were added after stimulation with PMA. Starred entries are different from control, P<0.05.

Influence of PR-39 peptides on neutrophil chemotaxis. Chemotaxis of porcine neutrophils was measured by the procedure of Salak et al. (1993). Briefly, PR-39 or its truncated analogs (30 μl in Dulbecco's Modified Eagle's medium) were placed in the bottom chamber of a modified Boyden chamber (Neuro Probe, Cabin John, Md.) and porcine neutrophils (50 μl at $5\times10^6$ cells/ml) were placed in the top chamber. The chambers were incubated at 37° C. for 30 min. Cells that migrated through the porous membrane (pore size 5 μm) were stained using LeukoStat solution and enumerated. Five microscope fields were counted and the cells that migrated through the membrane were standardized to the medium control and referred to as the migration index. PR-15, PR-14, PR-16, and PR-26 were used at 1 μM; PR-39 was used at 0.05 μM. The chemoattractant, C5a at $10^{-8}$ M, was used as a positive control. Starred entries are different from the control, P<0.05.

Influence of PR-39 and PR-26 on intestinal epithelial cells. A nonradioactive assay based on the cellular conversion by viable cells of a tetrazolium salt into a blue formazan product was used to determine if PR-39 or PR-26 were toxic to intestinal epithelial cells. Ninety-six-well microtiter plates were seeded with the rat intestinal epithelial cell line, IEC-6, ($5\times10^4$ cells/well) in DMEM containing 10% fetal bovine serum, 1% antibiotic/antimycotic, and 0.1 bovine insulin, and incubated at 37° C. for three days to achieve confluency. Cells then were incubated with different concentrations of PR-26 or PR-39 in medium without antibiotic/antimycotic for three days. Well contents then were aspirated and monolayers were washed with medium. Medium (100 μl) and 15 μl of dye solution (Promega, Wis.) were added to each well and plates were incubated for 4 hr. at 37° C. Solubilization buffer (100 μl, Promega, Wis.) was added to each well and plates were incubated overnight to allow solubilization of the formazan crystals. Absorbance then was read at 570 nm using a microplate reader.

Results and discussion

Figure 2:
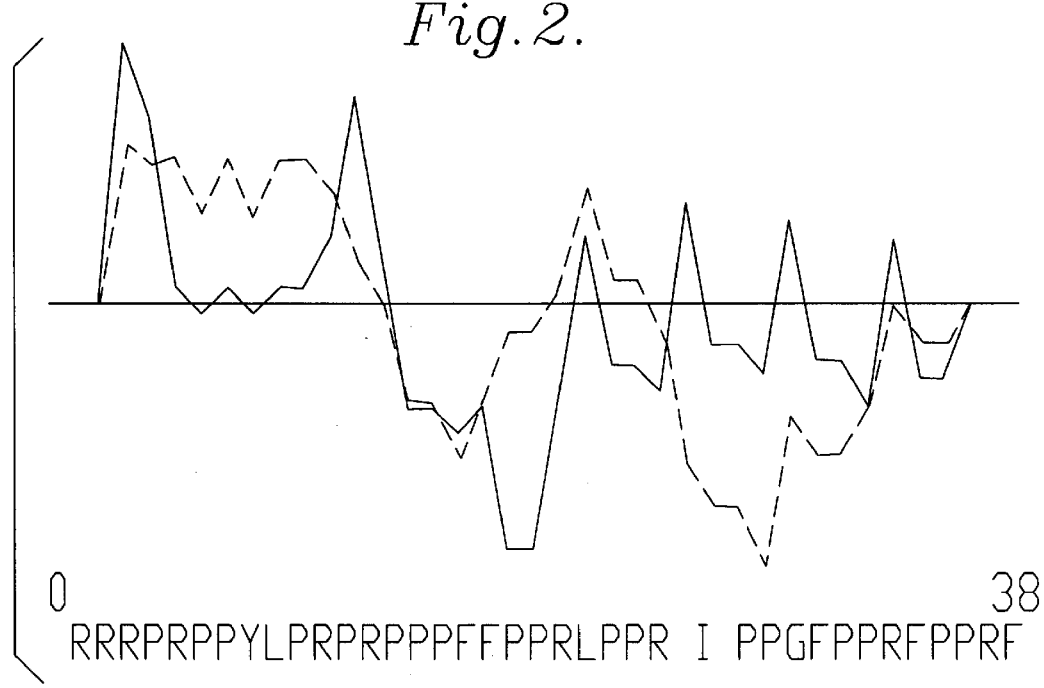
FIG. 2 is a graphic Parker et al. protein hydrophilicity (solid line) and antigenicity (dashed line) scale for PR-39 wherein the hydrophilic and antigenic domains are above the horizontal line and the hydrophobic domains are below the horizontal line.

Peptide Design and Synthesis. PR-39 and four analogs were synthesized and named PR-39 (whole molecule), PR-26 ($NH_2$-terminal segment 1 to 26), PR-16 (central segment 11 to 26), PR-15 (COOH-terminal segment 25 to 39), and PR-14 ($NH_2$-terminal segment 1 to 14). Peptide sequences are illustrated in FIG. 1 using the single letter amino acid code, and PR-39 and PR-26 are identified as SEQ ID NO: 1 and SEQ ID NO: 2, respectively. Rationale for design of the peptides was based on the graphic protein hydrophilicity scale (FIG. 2), because the hydrophilicity profile indicates locations of important interaction sites, such as antibody and receptor binding sites (Hopp, 1985). PR-26 was designed to mimic the hydrophilicity profile of PR-39 which has a hydrophilic $NH_2$-terminus and a hydrophobic COOH-terminus. As most endogenous antibacterial peptides are cationic molecules, PR-14, the highest positively charged segment (43% vs 25% of whole molecule), was designed to test if cationicity itself was enough for antibacterial activity. The central domain, PR-16, having the average positive charge intensity (25%) was synthesized as the control for PR-14. PR-15, the COOH-terminus of PR-39 was designed to determine if it was one of the functional domains of PR-39.

Figures 3, 4:
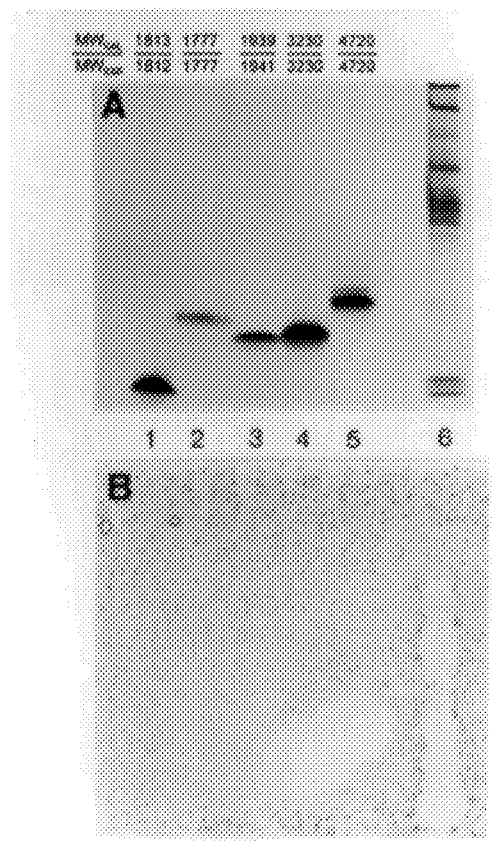
FIG. 3 is a photograph of the AU-PAGE analysis of synthetic peptides wherein each lane contains ten micrograms of peptide, lane 1=PR-14, lane 2=PR-15, lane 3=PR-16, lane 4=PR-26, lane 5=PR-39 and lane 6=neutrophil granule extract, with calculated molecular weight (MW$_{cal}$) over the experimental mass spectrometry data (MW$_{exp}$) listed over each lane for the respective synthetic peptides.
FIG. 4 is a photograph of a gel overlay assay wherein an AU-PAGE analysis was conducted as described in FIG. 3 and after electrophoresis, the gel was washed, overlaid with bacteria (E. coli) in agarose, cultured (18 hr. at 37° C.) and stained with 0.3% amido black.

Calculated molecular weights and experimental determinations of the mass of the synthetic peptides suggested that these peptides possessed the designed sequences (1813, 1777, 1939, 3230, and 4720 calculated molecular weight vs 1812, 1777, 1941, 3230, and 4720 experimental determination of mass for PR-14, PR-15, PR-16, PR-26, and PR-39, respectively). Synthetic peptides (>95% purity in RP-HPLC) were subjected to AU-PAGE to further determine the purity and charge intensity (FIG. 3). In this analysis, 10 micrograms of peptide were dissolved in 20 microliters of sample buffer (3 M urea with 5% acetic acid) and subjected to AU-PAGE. Samples were run with 5% acetic acid at 150 volts for approximately 15 min. or until the dye front (methyl green) had migrated to the end of the gel. The gel was stained with 0.3% amido black.

As expected, PR-14 migrated in the front because it has the highest positive charge intensity, and PR-15, having the lowest positive charge intensity, migrated far behind PR-14 even though its mass is slightly less than PR-14. Because PR-26 and PR-16 are smaller molecules than PR-39, they migrated faster than the parent molecule. Native PR-39 and synthetic PR-39 behaved identically in AU-PAGE and RP-HPLC analyses (data not shown).

Antibacterial Activity.

Gel-overlay and lawn-spotting assay. In the gel-overlay bactericidal assay, only PR-39 and PR-26 were found to have antibacterial activity against *E. coli* (FIG. 4, where the clear zones indicate antibacterial activity). In the "lawn-spotting" antibacterial assay, PR-39, PR-26, PR-16, PR-15 and PR-14 (FIG. 5), and the combination of PR-14 and PR-16, and PR-15 (data not shown) were tested; only PR-39 and PR-26, had antibacterial activity, all of the other segments and their mixtures showed no antibacterial activity even at 1 mg/ml. The FIG. 5 assay depicts an *S. typhimurium* plate where position 1 is a medium control (0.01% acetic acid); positions 2, 3 and 4 represent PR-14, PR-15 and PR-16 at 1 mg/ml in 0.01% acetic acid, respectively; positions 5 and 6 represent PR-26 at 100 micromole and 50 micromole in PBS; positions 7, 8, 9 and 10 represent PR-26 at 100, 50, 25 and 10 micromoles in 0.01% acetic acid; positions 11, 12 and 13 represent PR-39 at 100, 50 and 25 micromoles in 0.01% acetic acid; and the clear zones indicate antibacterial activity.

Figure 5:
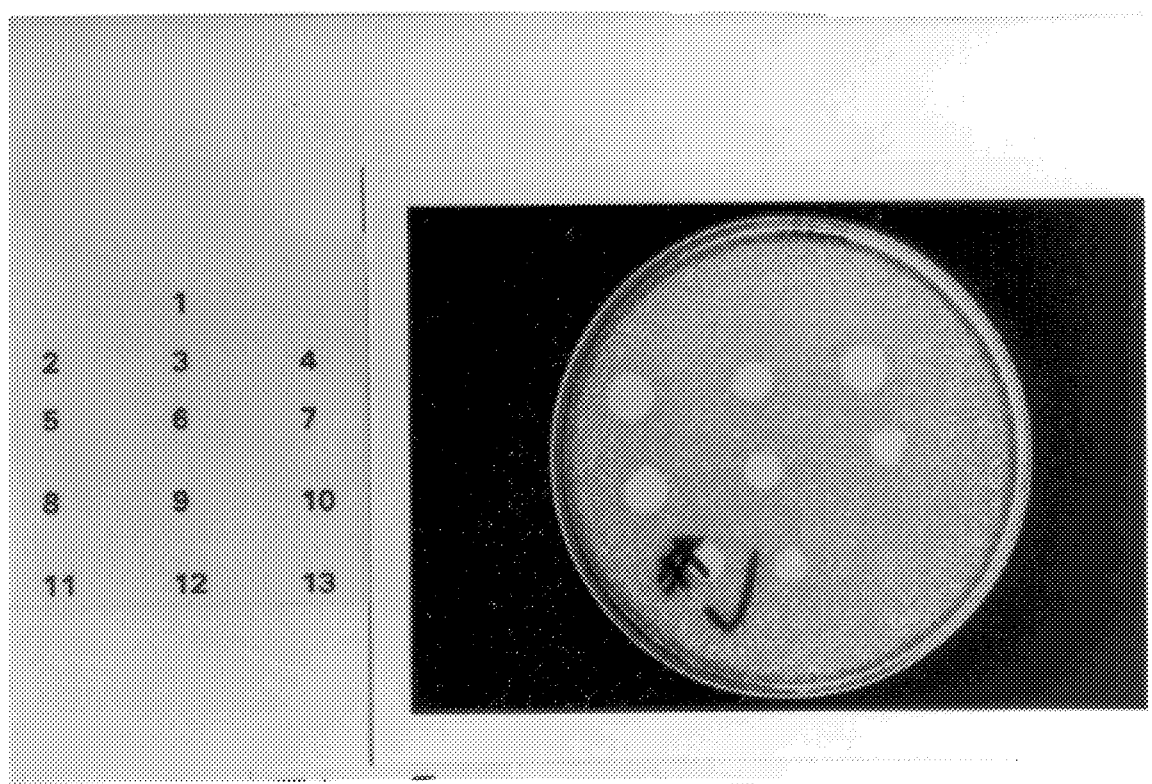
FIG. 5 is a photograph depicting the results of an antibacterial "lawn-spotting" assay wherein the spot positions are numbered on the left of the photograph.

These results suggest that: 1) the very cationic $NH_2$-terminus of PR-39 is not sufficient for antibacterial activity; 2) the COOH-terminus does not contribute to the antibacterial activity of PR-39; 3) PR-26, the $NH_2$-terminal segment 1 to 26, is the antibacterial domain of PR-39; and 4) certain secondary structure conformation is required for the antibacterial activity of PR-39 and PR-26 since segment mixtures did not have any antibacterial activity. The "lawn-spotting" assay also showed that PR-26 had greater antibacterial activity against *E. coli* and *S. typhimurium* than PR-39 (FIG. 5).

Figure 6:
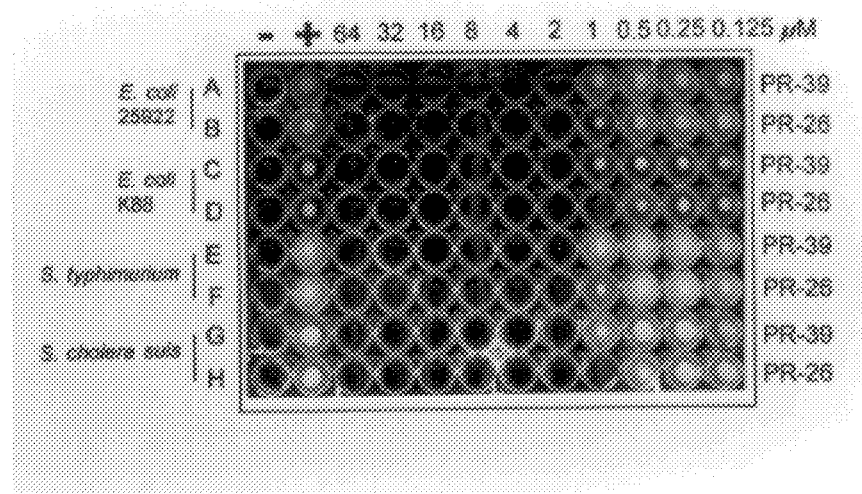
FIG. 6 is a photograph of a 96-well microtiter plate used to determine the minimal inhibitory concentration of PR-39 and PR-26 against enteric bacteria.

Minimal inhibitory concentration (MIC) and minimal bactericidal concentration (MBC). The MIC of PR-39 and PR-26 for *E. coli*, 25922; *E. coli*, K88; *Salmonella typhimurium*; *Salmonella cholerasuis*; *Streptococcus suis*; and *Staphylococcus aureus* are shown in FIG. 6 and Table 1. For the enteric, Gram-negative bacteria, the MIC of PR-39 and PR-26 ranged from 1 to 4 μM; PR-26 had a lower MIC than PR-39. Similarly, the MBC of PR-26 were the same or lower than the MBC of PR-39 and ranged from 2 to 8 μM for the Gram-negative bacteria (Table 1). These findings suggest that PR-26 may be an effective antibiotic against enteric, Gram-negative bacteria such as *E. coli* or *Salmonella*. Table 1. Minimal inhibitory concentration, μM (MIC) and minimal bactericidal concentration, μM (MBC) of PR-39 and PR-26 against six strains of bacteria.

| Bacteria | MIC | | MBC | |
|---|---|---|---|---|
| | PR-39 | PR-26 | PR-39 | PR-26 |
| *Escherichia coli*, 25922 | 4 | 2 | 8 | 8 |
| *Escherichia coli*, K88 | 2 | 1 | 4 | 4 |
| *Salmonella typhimurium* | 4 | 2 | 4 | 2 |
| *Salmonella cholerasuis* | 2 | 1 | 4 | 2 |
| *Streptococcus suis* | >64 | 16 | >64 | >64 |
| *Staphylococcus aureus* | >250 | >250 | ND* | ND* |

*Not determined

Figure 7:
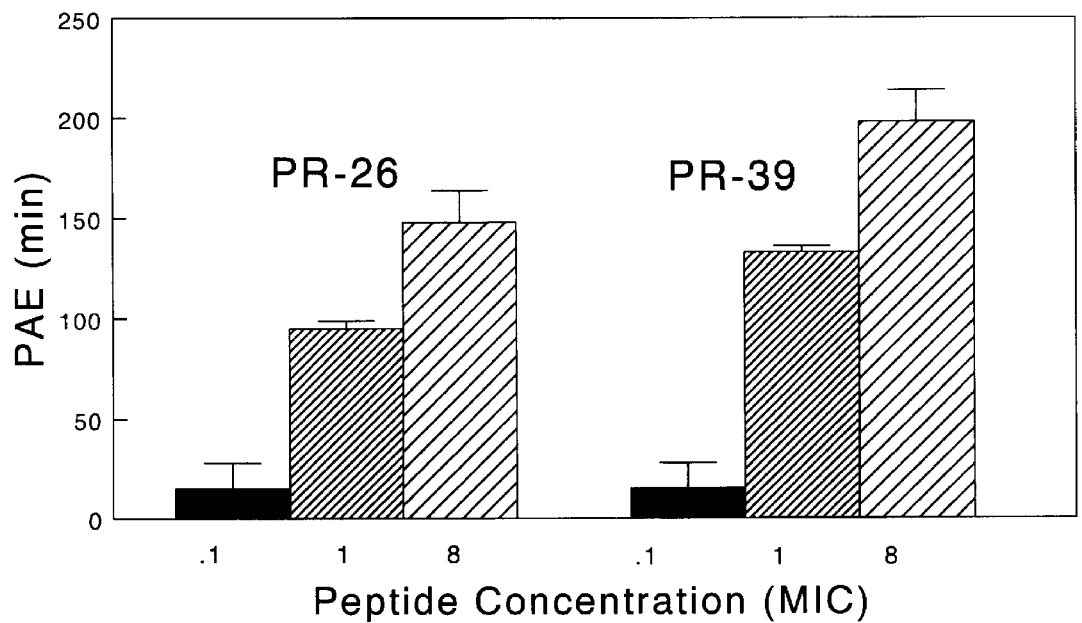
FIG. 7 is a graph illustrating the postantibiotic effect of PR-39 and PR-26 against S. typhimurium.

Postantibiotic effect (PAE). The relationship between peptide concentration and the duration of PAE of PR-39 and PR-26 is shown in FIG. 7. Suboptimal peptide concentrations (0.1 MIC) only caused a slight growth delay in both PR-39—and PR-26—treated bacteria. However, at 1 and 8 MIC PAE against *S. typhimurium* was significantly increased. These findings agree with other antibacterial data and shows clearly that PR-26 limits the growth of enteric bacteria.

Figure 8:
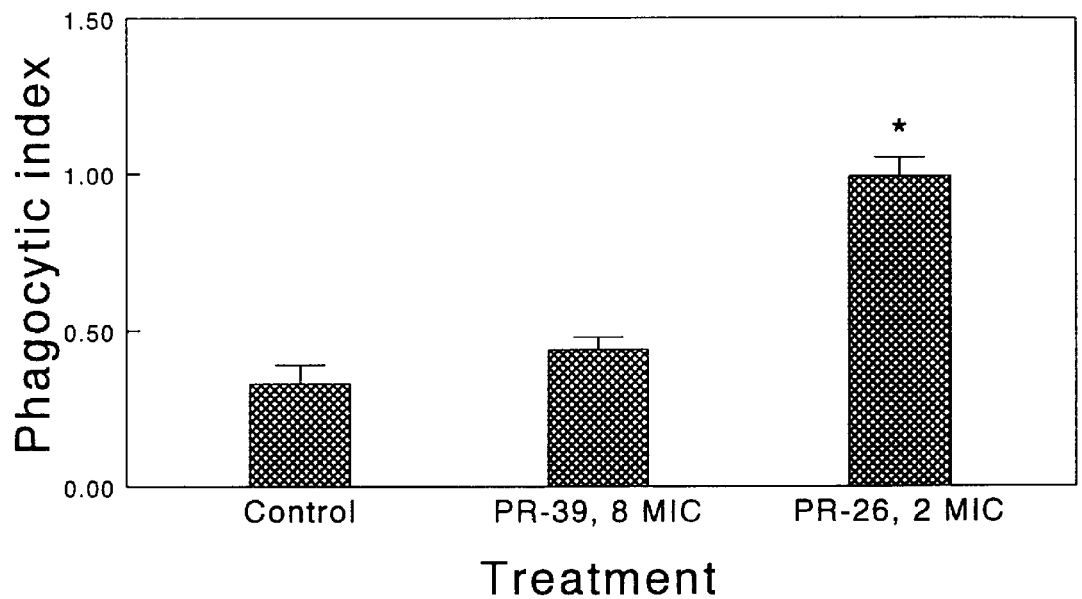
FIG. 8 is a graph illustrating the phagocytic susceptibility of S. cholerasuis after exposure to PR-26 and PR-39.

Susceptibility to neutrophil phagocytosis. Bacteria treated with PR-26 were more susceptible to neutrophil phagocytosis (FIG. 8). A 10 min. exposure of *Salmonella cholerasuis* to 2 MIC of PR-26 significantly increased the capability of porcine neutrophils to phagocytose the bacteria. Treatment of *Salmonella cholerasuis* with PR-39 at 8 MIC did not increase the phagocytic index of porcine neutrophils. Neutrophils phagocytosed both single and filamentous bacteria. These data show that, in addition to the direct antibacterial activity of PR-26, this antibacterial peptide predisposes enteric bacteria to elimination by phagocytic cells. This property suggests that PR-26 works synergistically with the host's immune system to limit enteric bacterial growth.

Figure 9:
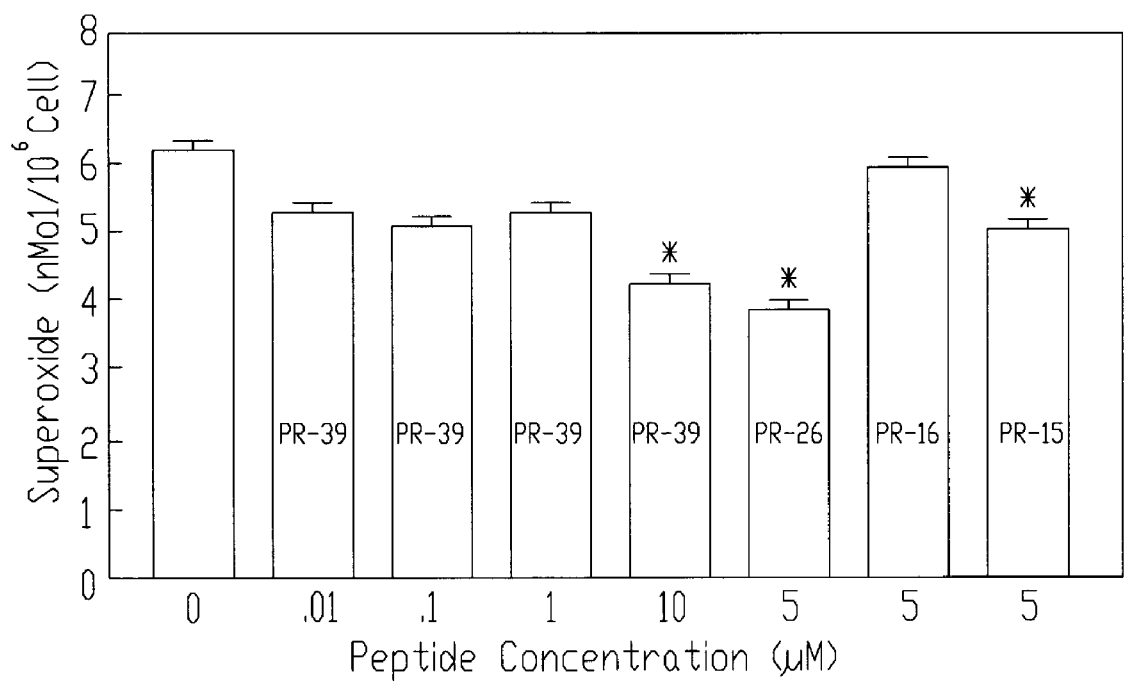
FIG. 9 is a graph illustrating the regulation of superoxide production of porcine neutrophils in the presence of PR-peptides.

Regulation of neutrophil superoxide anion production by PR-39 and PR-26. Generation of reactive oxygen intermediates, such as superoxide anion, is a means by which phagocytic cells kill microorganisms. However, these toxic molecules can also damage tissues and cells of the host and have been implicated in the generation of diseases such as bronchial asthma (Kilpatrick, et al., 1995). Neutrophils incubated with 5 μM of PR-26 produced significantly less superoxide anion than control cells (3.86+0.64 vs 6.29+0.12 nM/$10^6$ cells/20 min). PR-26 was more effective than PR-39 in decreasing neutrophil production of superoxide anion (FIG. 9). These findings suggest that PR-26 may be useful as a prophylactic treatment in diseases such as bronchial asthma, where reactive oxygen intermediates induce tissue damage.

Figure 10:
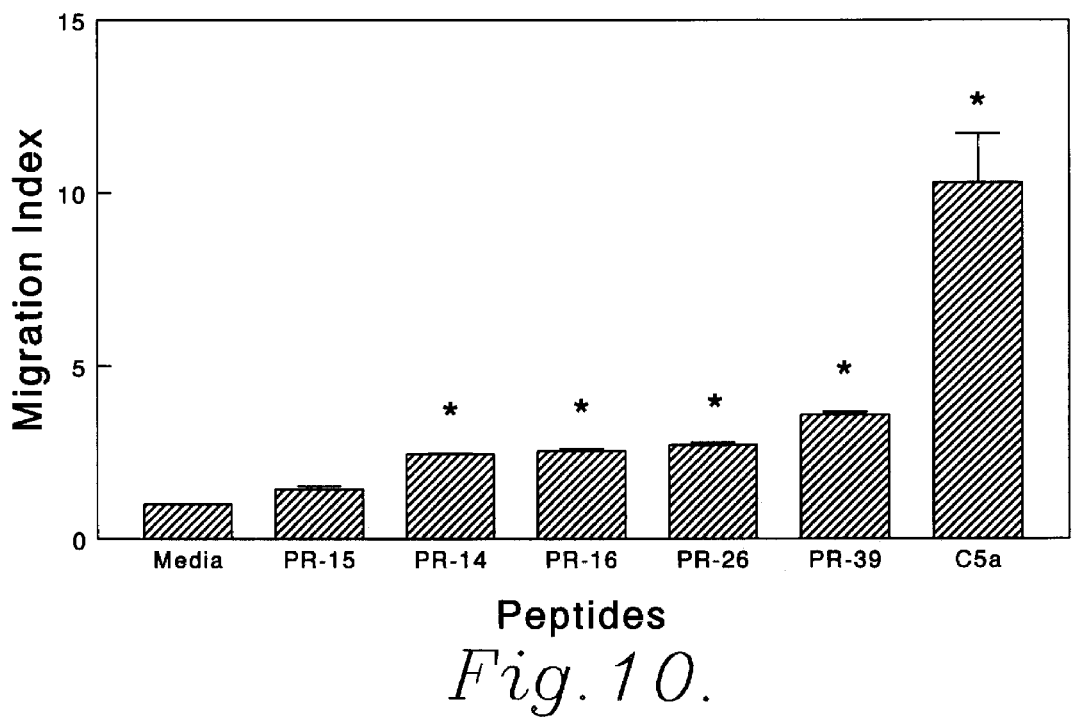
FIG. 10 is a graph depicting the chemotaxis of porcine neutrophils by PR-39 and analogs thereof.

Influence of PR-39 peptides on neutrophil chemotaxis. Phagocytic cells migrate from the blood to areas of inflammation in response to chemotactic agents. FIG. 10 shows that PR-26 and several of the other synthetic PR peptides are chemotactic agents for neutrophils. The ability of PR-26 to function as a chemotactic agent increases the probability that sufficient phagocytic cells are present at an inflammatory site to limit an infection.

Figure 11:
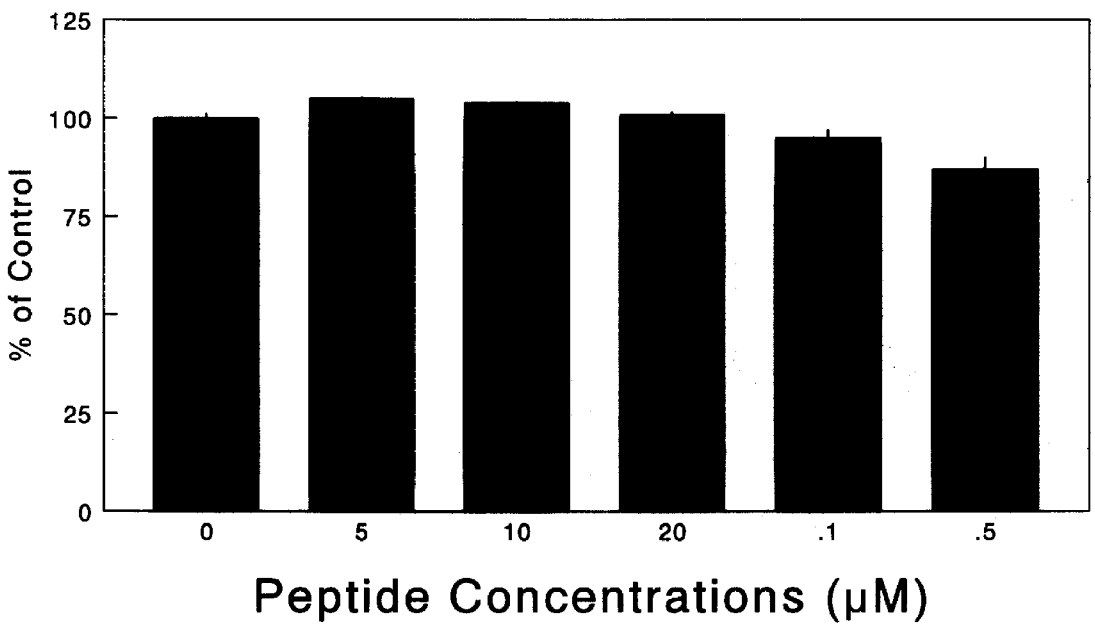
FIG. 11 is a graph illustrating the cytotoxicity of PR-26 and PR-39 in intestinal epithelial cells.

Influence of PR-39 and PR-26 on intestinal epithelial cells. FIG. 11 shows the cytotoxic activity of PR-39 and PR-26 on rat small-intestine epithelial cells (IEC-6). PR-26 was not cytotoxic to IEC-6 cells even at concentrations (20 μM) much greater than the MIC for this peptide. However, IEC-6 cells were sensitive to PR-39 as cytotoxicity occurred at 0.5 μM, which is lower than the MIC for this peptide. These data show that PR-26 does not damage cells of the small intestine and should, therefore, be a safe oral antibiotic.

Taken together, these data suggest that PR-26 is the functional antibacterial domain of PR-39. In addition to its potent antibacterial activity against enteric pathogens, PR-26 showed significant postantibiotic effects and increased the susceptibility of bacteria to neutrophil phagocytosis. This novel antibacterial peptide was chemotactic for neutrophils, decreased the generation of superoxide anion production, and was not toxic to intestinal epithelial cells. These findings suggest that PR-26 is an effective antimicrobial for intestinal pathogens, such as *E. coli* and *Salmonella*.

REFERENCES

The following references are incorporated by reference herein.

Agerberth, B., Lee, J. Y., Bergman, T., Boman, H. G., Mutt, V., Tornvall, H. (1991) Amino acid sequence of PR-39: isolation from pig intestine of a new member of the family of proline-arginine-rich antibacterial peptides. *Eur. J. Biochem.* 202, 849–854.

Boman, H. G. (1991) Antibacterial peptides: key components needed in immunity. *Cell* 65, 205–207.

Boman, H. G., Agerberth, B., Boman, A. (1993) Mechanisms of action on *Escherichia coli* of cecropin P1 and PR-39, two antibacterial peptides from pig intestine. *Infect. Immun.* 61, 2978–2984.

Gabay, J. E. (1994) Ubiquitous natural antibiotics. *Science* 264, 373–374.

Gallo, R. L., Ono, M., Povsic, T., Page, C., Eriksson, E., Klagsbrun, M., Bernfield, M. (1994) Syndecans, cell surface heparan sulfate proteoglycans, are induced by a proline-rich antimicrobial peptides from wounds. *Proc. Natl. Acad. Sci. USA* 91, 11035–11039.

Gennaro, R., Skerlavaj, B., Romeo, D. (1989) Purification, composition, and activity of two bactenecins, antibacterial peptides of bovine neutrophils. *Infect. Immun.* 57, 3142–3146.

Hopp, T. P. (1985) Prediction of protein surfaces and interaction sites from amino acid sequences. In: Synthetic Peptides in Biology and Medicine, K. Alitalo, P. Partanen, A. Vaheri, Eds. pp. 3–12, Elsevier Science Publishers.

Kilpatrick, L. E., Jakabovics, E., McCawley, L. J., Kane, L. H., Korchak, H. M. (1995) Cromolyn inhibits assembly of the NADPH oxidase and superoxide anion generation by human neutrophils. *J. Immunol.* 154, 3429–3436.

Lee, J.-Y., Boman, A., Chuanxin, S., Andersson, M., J ornvall, H., Mutt, V., Boman, H. G. (1989) Antibacterial peptides from pig intestine: isolation of a mammalian cecropin. *Proc. Natl. Acad. Sci. USA* 86, 9159–9162.

Lehrer, R. I., Lichtenstein, A. K., Ganz, T. (1993) Defensins: antimicrobial and cytotoxic peptides of mammalian cells. *Annu. Rev. Immunol.* 11, 105–128.

Litteri, L., Romeo, D. (1993) Characterization of bovine neutrophil antibacterial polypeptides which bind to *Escherichia coli*. *Infect. Immun.* 61, 966–969.

Maloy, W. L., Prasad Kari, U. (1995) Structure-activity studies on magainins and other host defense peptides. *Biopolymers (Peptide Science)* 37, 105–122.

MacKenzie, F. M., Gould, I. M. (1993) The postantibiotic effect. *J. Antimicrobial Chemotherapy* 32, 519–537.

Moore, K. S., Bevins, C. L., Tomassini, N., Huttner, K. M., Sadler, K., Moreira, J. E., Reynolds, J., Zasloff, M. (1992)

A novel peptide-producing cell in *Xenopus*: multinucleated gastric mucosal cell strikingly similar to the granular gland of skin. *J. Histochem. Cytochem.* 40, 367–378.

National Committee for Clinical Laboratory Standards. Methods for Dilution Antimicrobial Susceptibility Tests for Bacteria that Grow Aerobically, 2nd Ed.; Approved Standard NCCLS Document M7-A2, Vol 10, No. 8.

Salak, J. L., McGlone, J. J., Lyte, M. (1993) Effects of in vitro adrenocorticotrophic hormone, cortisol and human recombinant interleukin-2 on porcine neutrophil migration and luminol-dependent chemiluminescence. *Vet. Immunol. Immunopathol.* 39, 327–337.

Shi, J., Goodband, R. D., Chengappa, M. M., Nelssen, J. L., Tokach, M. D., McVey, D. S., Blecha, F. (1994a) Influence of interleukin-1 on neutrophil function and resistance to *Streptococcus suis* in neonatal pigs. *J. Leukco. Biol.* 56, 88–94.

Shi, J., Ross, C. R., Chengappa, M. M., Blecha, F. (1994b) Identification of a proline-arginine-rich antibacterial peptide from neutrophils that is analogous to PR-39, an antibacterial peptide from the small intestine. *J. Leukco. Biol.* 56, 807–811.

Steiner, H., Hultmark, D., Engström, A. Bennich, H., Boman, H. G. (1981) Sequence and specificity of two antibacterial proteins involved in insect immunity. *Nature* 292, 246–248.

Zasloff, M. (1987) Magainins, a class of antibacterial peptides from *Xenopus* skin: isolation, characterization of two active forms, and partial cDNA sequence of a precursor. *Proc. Natl. Acad. Sci. USA* 84, 5449–5543.

Zasloff, M. (1992) Antibiotic peptides as mediators of innate immunity. *Current Opin. Immunol.* 4, 3–7.

---

We claim:

1. The isolated peptide compound consisting of SEQ ID NO: 2.

2. A method of inhibiting microbial growth in an environment capable of sustaining such growth comprising administering to said environment a microbial growth-inhibiting amount of the peptide compound consisting of SEQ ID NO: 2.

* * * * *

UNITED STATES PATENT AND TRADEMARK OFFICE
CERTIFICATE OF CORRECTION

PATENT NO. : 5,830,993
DATED : November 3, 1998
INVENTOR(S) : Frank Blecha and Jishu Shi It is certified that error appears in the above-identified patent and that said Letters Patent is hereby corrected as shown below:

<u>Title page,</u>
Please insert the following paragraph:

-- Federally Sponsored Research or Development
     This invention was made with government support under Grant 93-37206-9351 awarded by the United States Department of Agriculture. The government has certain rights in the invention. --

Signed and Sealed this

Fifth Day of March, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 39 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Arg  Arg  Arg  Pro  Arg  Pro  Pro  Tyr  Leu  Pro  Arg  Pro  Arg  Pro  Pro  Pro
1                   5                        10                       15

Phe  Phe  Pro  Pro  Arg  Leu  Pro  Pro  Arg  Ile  Pro  Pro  Gly  Phe  Pro  Pro
               20                       25                       30

Arg  Phe  Pro  Pro  Arg  Phe  Pro
               35
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Arg  Arg  Arg  Pro  Arg  Pro  Pro  Tyr  Leu  Pro  Arg  Pro  Arg  Pro  Pro  Pro
1                   5                        10                       15

Phe  Phe  Pro  Pro  Arg  Leu  Pro  Pro  Arg  Ile
```